United States Patent [19]

Bosman et al.

[11] Patent Number: 5,574,181
[45] Date of Patent: Nov. 12, 1996

[54] PROCESS FOR THE PREPARATION OF AN AMINOITRILE BY PARTIAL HYDROGENATION OF A NITRILE COMPOUND WITH TWO OR MORE NITRILE GROUPS

[75] Inventors: Hubertus J. M. Bosman, Sittard; Franciscus H. A. M. J. Vandenbooren, Maastricht, both of Netherlands

[73] Assignee: DSM N.V., Heerlen, Netherlands

[21] Appl. No.: 256,061

[22] PCT Filed: Dec. 17, 1992

[86] PCT No.: PCT/NL92/00230

§ 371 Date: Aug. 17, 1994

§ 102(e) Date: Aug. 17, 1994

[87] PCT Pub. No.: WO93/12073

PCT Pub. Date: Jun. 24, 1993

[30] Foreign Application Priority Data

Dec. 18, 1991 [NL] Netherlands ............................ 9102112

[51] Int. Cl.$^6$ ............................................... C07C 253/30
[52] U.S. Cl. ................................................... 558/459
[58] Field of Search ............................................. 558/459

[56] References Cited

U.S. PATENT DOCUMENTS 1,628,190  5/1927  Raney.
4,362,671  12/1982  Diamond et al. ................. 564/490 X
5,151,543  9/1992  Ziemecki ........................... 558/459

FOREIGN PATENT DOCUMENTS 0077911   5/1983   European Pat. Off..
A10077911 5/1983   European Pat. Off..
1325153   8/1973   United Kingdom .................. 558/459
WO-92/21650 12/1992 WIPO ................................. 558/459

OTHER PUBLICATIONS

Mares, et al., Journal of Catalysis, 112, (1988), pp. 145–156.
Tomalia et al, *Agnew. Chem. Int. Ed. Engl.*, 29:138–175 (1990).
Handbook of Chemistry and Physics, 59th Ed., CRC Press, 1978–1979.
Montgomery, Functional Group Activity of Promoted Raney Nickel Catalysts, *Catalysis of Organic Reactions*, 5:383–409 (1981).
Mares, Preparation and Characterization of a Novel Catalyst for the Hydrogenation of Dinitriles to Aminonitriles, *Journal of Catalysis*, 112:145–156 (1988).

*Primary Examiner*—Johann Richter
*Assistant Examiner*—Laura R. Cross
*Attorney, Agent, or Firm*—Cushman Darby & Cushman, L.L.P.

[57] ABSTRACT

The invention relates to a process for the preparation of an aminonitrile by partially hydrogenating a nitrile compound with two or more nitrile groups in the presence of a catalyst which contains a metal from group 8 of the periodic system of the elements, the hydrogenation being carried out under water-free reaction conditions and the catalyst having been treated with an alkanolate. Preferably, the catalyst is a Raney nickel or Raney cobalt catalyst which has been pretreated with an alkali metal alkanolate or an earth alkali metal alkanolate such as sodium or potassium methanolate.

34 Claims, No Drawings

PROCESS FOR THE PREPARATION OF AN AMINOITRILE BY PARTIAL HYDROGENATION OF A NITRILE COMPOUND WITH TWO OR MORE NITRILE GROUPS

FIELD OF THE INVENTION

This application is a 371 of PCT/NL92/00230, filed Dec. 17, 1992.

The invention relates to a process for the preparation of an aminonitrile by partially hydrogenating a nitrile compound with two or more nitrile groups in the presence of a catalyst which contains a metal from group 8 of the periodic system of the elements.

BACKGROUND OF THE INVENTION

Such a process is known from F. Mares, J. E. Galle, S. E. Diamond and F. J. Regina, Journal of Catalysis 112, (1988), pp. 145–156, according to which publication an alkane dinitrile, such as α,ω-butane dinitrile (succinonitrile), is hydrogenated in the presence of a catalyst consisting of finely divided rhodium halogenide on a magnesium oxide carrier. The catalyst is pretreated with sodium hydroxide, yielding metallic rhodium on a magnesium oxide carrier. During the hydrogenation reaction $NH_3$ is supplied in an excess relative to the dinitrile. In the hydrogenation of succinonitrile, at a reaction temperature of 100° C., a pressure of 50 atm (5 MPa) and a reaction time of 5.5 hours, a conversion of 89.4% and a selectivity to aminobutyronitrile of 87.3% is achieved. This corresponds to an aminobutyronitrile yield of 78%. Although this yield is high, a further increase in the yield is desirable. In addition to this, a large amount of undesirable by-product is formed (11.9% of the succinonitrile being converted into dimers and oligomers). The article also reports an ε-amino capronitrile yield of 66.6% from adiponitrile at 90% conversion. Dimers are formed in an amount of 2.7%.

SUMMARY AND OBJECTS OF THE INVENTION

It is the object of the present invention to provide a process for the preparation of an aminonitrile by means of a simple method, at a high reaction velocity and with a high aminonitrile yield, in which the formation of undesirable by-products is limited.

The object of the present invention is achieved in that the hydrogenation is carried out under virtually water-free reaction conditions and the catalyst has been treated with an alkanolate.

Surprisingly, it has been found that according to the present invention, aminonitrile yields in excess of 80% can be attained. Moreover, in the process of the invention there is no need to supply $NH_3$ during the reaction. As byproduct virtually only oligoamine is formed, which can be worked up in the chemical industry, as opposed to dimers and oligomers, which are formed according to the process known from the art.

DETAILED DESCRIPTION OF THE INVENTION

The process according to the present invention involves preparing an aminonitrile by partially hydrogenating a nitrile compound having at least two nitrile groups with hydrogen under almost water-free reaction conditions in the presence of a catalyst. The catalyst contains a metal from group 8 of the Periodic Table of Elements and the catalyst has been treated with an alkanolate.

The process according to the invention is suitable for the partial hydrogenation of any nitrile compound with two or more nitrile groups.

Thus, for instance, α,ω-alkane dinitriles are suitable for conversion to their corresponding aminonitriles using the process according to the present invention. These alkane dinitriles are of a general formula $NC-(CH_2)_n-CN$, n being an integer from 0 to 12. Preferably, n is an integer from 1 to 6. Examples are: malonitrile (n=1), succinonitrile (n=2), adiponitrile (n=4) and glutaronitrile (n=5). The process according to the present invention is particularly suitable for the hydrogenation of succinonitrile and adiponitrile.

The hydrogenation of α,ω-alkane dinitriles can be represented by the following reaction scheme:

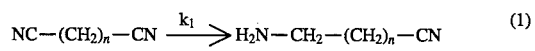  (1)

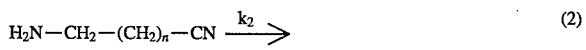  (2)

$$H_2N-CH_2-(CH_2)_n-CH_2-NH_2$$

In this scheme the product of reaction (1) is the desired ω-aminoalkanenitrile, which can react further to form diamines in the presence of hydrogen according to reaction (2). $k_1$ and $k_2$ denote the rate constants of reactions (1) and (2). In a selective hydrogenation to the ω-amino alkane nitrile the ratio $k_1/k_2$ is high.

The process according to the present invention is also suitable for the partial hydrogenation of compounds containing more than two nitrile groups, for instance for compounds with 3–12 carbon atoms with three or four nitrile groups. The invention is particularly suitable for the hydrogenation of dendritic macromolecules which contain nitrile groups. A general description of dendritic macromolecules can be found, for instance, in D. A. Tomalia et al. in Angew. Chem. Int. Ed. Engl. 29, (1990) pp. 138–175. These macromolecules as a rule have a weight-average molecular weight ($M_w$) of 100–100,000 kg/kmol. Examples of dendritic macromolecules that are suitable for the partial hydrogenation are compounds of the formula:

  (3)

where m and n are positive integers, the latter standing for the number of branches of the dendritic macromolecule, while m is higher than or equal to n. The symbols in formula (3) denote the following:

K a chemical compound that forms the nucleus of the dendritic macromolecule

RX branches linked to the nucleus which contain carbon atoms and optionally hetero atoms R'CN a terminal branch with a nitrile group.

According to the present invention the compounds according to formula (3) can be partially hydrogenated according to the reaction equation:

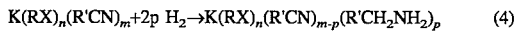  (4)

where p is a positive integer. The degree of partial hydrogenation Q is defined as:

$$Q = p/m \quad (5)$$

According to the invention Q is lower than 1, preferably lower than 0.75. After partial hydrogenation the dendritic macromolecules can be built up further through reaction with compounds that react with the nitrile or amine groups. This may again be followed by partial hydrogenation and the process of alternate buildup or growth and partial hydrogenation can be repeated several times. Since the dendritic macromolecule is built up solely at the location of either the terminal amine groups or the terminal nitrile groups, while according to the invention the degree of hydrogenation can be controlled by changing the reaction conditions, the structure of the dendritic macromolecule can be influenced in any desired way.

The partial hydrogenation according to the invention has to be carried out under almost water-free reaction conditions, which is understood to mean that the reaction medium contains less than 5 wt. % water. The water content is determined by means of a Karl Fischer titration according to the ASTM-E 203 (1971) standard. Preferably, the water content is below 1 wt. %, more preferably below 0.5 wt. %, and in particular below 0.1 wt. %.

The nitrile can be dissolved in a suitable solvent prior to the hydrogenation. The solvents that can be used according to the invention should contain almost no water, the water content of the reaction medium, as stated above, being the criterion. Examples of suitable solvents are tetrahydrofuran, dioxane, alkane (di)amines, alcohols and ethers. Solvents that are particularly suitable are the α-ω-alkane diamines or alcohols with 1–10 C atoms. Examples of such particularly suitable solvents are diamino-ethane, diaminobutane, diaminohexane, methanol, ethanol, n-propanol, i-propanol and n-butanol.

The hydrogenation is effected with hydrogen gas ($H_2$). This is usually present as a gas phase, which is in contact with the solution containing the nitrile, a small portion of the hydrogen gas being dissolved in the solution. The partial pressure of hydrogen is at least 1 atm (0.1 MPa), but usually 5–500 atm (0.5–50 MPa). In particular 30–100 atm (3–10 MPa), hydrogen pressure is applied. These and all other pressures are stated as absolute pressures. Other gases may be present during the reaction, but they are usually present in small amounts.

During the hydrogenation hydrogen is preferably present in a molar ratio of $H_2$: nitrile of at least 1. Hydrogen consumed in the reaction is usually supplied during the reaction. As a rule, the hydrogen pressure is kept constant during the entire reaction.

The temperature during the hydrogenation is not critical, but is usually 0°–200° C., and in particular 20°–100° C.

The catalyst applied according to the invention is a catalyst that contains a metal from group 8 of the periodic system of the elements which has been treated with an alkanolate. The periodic system of the elements is understood to mean the table as printed on the cover of the Handbook of Chemistry and Physics, 58th Edition, CRC Press, 1977–1978.

Metals from group 8 are known to be active in the hydrogenation of nitriles (see, for instance, EP-A-0077911). Nickel, cobalt, platinum, palladium and rhodium are suitable choices. For sufficient catalytic activity, the metal must have a large contact area. The metal can be used as such or on a suitable support.

U.S. Pat. No. 4,362,671 describes a process for the partial hydrogenation of dinitriles to α,ω-aminonitriles using rhodium complexes of the formula (RR'Rh)A as a catalyst, in which R is derived from a non-allenic hydrocarbone diene of at least 4 carbons, R' is an organitrogen compound and A is a complex monovalent anion serving as counter-anion.

According to the present invention, Raney nickel or Raney cobalt are particularly suitable as a catalyst. A description of Raney catalysts and their preparation can be found in U.S. Pat. No. 1,628,190 (1927).

Raney nickel contains mainly nickel and aluminium, the latter in the form of metallic aluminium, aluminium oxides or aluminium hydroxides. Small amounts of other metals in elementary or in chemically bound form, such as iron and/or chromium, may be added to the Raney nickel to increase the activity and selectivity for the hydrogenation of certain groups of compounds. These added metals are usually called promoters, while the catalyst is called promoted Raney nickel. For the use of promoters, see: S. R. Montgomery, Catalysis of Organic Reactions 5, pages 383–409 (1981). According to the invention it is particularly preferred to use chromium and/or iron promoted Raney nickel as catalyst.

Raney cobalt also contains aluminium and may contain promoters. It is known, for instance, that chromium promoted Raney cobalt is suitable for the hydrogenation of nitriles to primary amines.

Examples of Raney catalysts that are suitable for the process according to the invention are the Raney nickel types Degussa BLM 112 W®, Grace 2400®, Activated Metals A-4000® and Doduco Ra/Ni® (Fe-Cr promoted) and Raney cobalt type Grace 2724®.

According to the present invention the catalyst is pretreated. Since the hydrogenation is to be carried out under almost water-free reaction conditions, the catalyst has to be freed of water. This can be effected using the methods known from the art, for instance by washing with a water-free solvent. Preferably, the water is removed from the catalyst before the catalyst is treated with the alkanolate.

According to the invention the catalyst is treated with an alkanolate. The alkanolate according to the invention is preferably an alkanolate with 1–10 C-atoms, for instance methanolate, ethanolate, n-propanolate, i-propanolate or n-butanolate. The alkanolate is usually available in the form of a metal salt. According to the invention alkali metal alkanolates or earth alkali metal alkanolates are particularly suitable. Examples of extremely suitable alkanolates are potassium and sodium methanolate. The amount of alkanolate applied to the catalyst is usually 0.01–0.5 g per g of catalyst, in particular 0.03–0.2 g/g catalyst, and more in particular 0.05–0.15 g/g catalyst.

The temperature during the treatment with alkanolate is not critical. Usually the treatment takes place at a temperature between 0° and 50° C., in particular at room temperature. The pressure during the treatment is of little importance. Usually the treatment takes place under atmospheric pressure. Preferably, the treatment takes place by mixing the catalyst intensively with a solution of the alkanolate. The solution is preferably a concentrated solution of the alkanolate in an alkanol. The concentration is, for instance, 5–1000 g/l, in particular 10–500 g/l.

The products that can be prepared according to the invention are widely applied as raw materials for the chemical or the pharmaceutical industry. Examples are the use of ω-aminobutane nitrile (aminobutyro nitrile) as a raw material for the preparation of the hydrochloride of γ-aminobutryramide (gabamide), with the formula ($H_2N$—$CH_2$)$_3$-$CONH_2$·HCl, which is used for the preparation of antidepressants. In addition, aminobutyro nitrile can be converted into pyrrolidone through saponification and ring closure.

ω-Aminoalkane nitriles can also find application as raw material for the production of nylons. Thus, ε-aminohexane nitrile (ε-aminocapronitrile) can be used as a raw material for ε-caprolactam, which serves as a raw material for nylon-6. In this route 1,4-dicyano butane (adiponitrile) is subjected to selective hydrogenation according to the invention to yield ε-amino-capronitrile, which is converted into 6-amino-hexanoic acid (ε-amino caproic acid) through saponification, which is subsequently converted into caprolactam by means of a ring closure reaction in which $H_2O$ is split off.

The dendritic macromolecules that can be prepared according to the invention can be used in electronics, for calibration of sieves, in catalyst carriers and for selective membranes and coatings. In addition, the dendritic compounds can be used as impact modifiers or as crosslinking agents in various plastics.

The invention will be further elucidated in the of examples and comparative experiments, without, however, being limited thereto.

The reaction products were analyzed using a gas chromatograph of the type Hewlett Packard HP5890®, with a column (type No. CP WAX 51) filled with polyethylene glycol, and hydrogen as carrier gas. Succinonitrile was analyzed by means of a separate gas chromatograph, type Chrompack 428A®, with the following column composition: 5% phenyl, 95% methyl polysiloxane, type CP SIL 8 CB, and nitrogen as carrier gas.

The amount of water in the reaction mixture was determined by means of a Karl Fischer titration according to ASTM-E 203 (1971).

EXAMPLE I

Raney nickel of the type Degussa BLM 112W® was used as a catalyst; according to the producer the composition was 85 wt. % Ni, 2.0 wt. % Fe, 2.5 wt. % Cr and 9.7 wt. % Al (Al and $Al2O_3$). 8 g (dry weight) of catalyst was washed five times with 25 ml water-free methanol, prepared by drying methanol with a type 3A molecular sieve. After sedimentation of the slurry, the methanol was decanted. The slurry was subsequently contacted with a solution of 0.8 g $NaOCH_3$ in 20 ml methanol, intensive stirring being applied. After sedimentation of the slurry, the liquid was decanted and the treated catalyst was washed with 25 ml diaminoethane, followed by decantation of the washing liquid.

As reactor a 160 ml Parr autoclave provided with a drain valve with a filter to trap the catalyst particles, was used. The reactor was further equipped with a 50 ml dosing vessel, connected to the autoclave via a dosing line with a valve. Both the reactor and the dosing valve have adjustable heating and pressure control. The reactor contents can be mixed by means of a stirrer.

The treated catalyst was introduced into the autoclave as a slurry in 80 g diamino-ethane. The water content of this catalyst slurry was 0.77 wt. %. Subsequently the autoclave was purged three times with $H_2$, the $H_2$ pressure was raised to 70 atm, and the temperature was raised to 80° C. while stirring (1500 rpm). 8 g succinonitrile was dissolved in 10 g diamino-ethane and introduced into the dosing vessel. Subsequently the dosing vessel was purged with $H_2$ twice and the pressure was raised to 80 atm with $H_2$. After this, the valve shutting off the dosing vessel was opened, so that the content of the dosing vessel are transferred to the autoclave, after which the reaction took place in the autoclave, under stirring (1500 rpm).

After 300 s the reaction was stopped, by opening the valve in the reactor drain so that the reactor contents, apart from the catalyst, flew out of the reactor. The product was analyzed by means of gas chromatography. The succinonitrile conversion was 100%. The reaction product consisted of: 85 mol % pyrrolidine, 14 mol % diaminobutane and 1 mol % pyrrolidine. The aminobutyronitrile yield was 85%.

COMPARATIVE EXPERIMENT A 8 g of the Raney nickel catalyst as in Example I was washed with 25 ml distilled water five times. After sedimentation of the slurry, the water was decanted. The slurry was subsequently contacted with a solution of 0.8 g NaOH in 20 ml distilled water, while stirring intensively. After sedimentation of the slurry, the liquid was decanted and the treated catalyst was washed with 25 ml diaminoethane. The water content of the catalyst slurry was 7.7 wt. %.

The catalyst thus treated was used in the hydrogenation of succinonitrile, as described in Example I. After 300 s 100% of the succinonitrile was converted. The reaction product consisted of 96 mol % diaminobutane and 2.5 mol % pyrrolidine and a residual amount of tarry product. The aminobutyro nitrile yield was 0%. Gas chromatographic analysis proved that the tarry product consisted mainly of diaminobutane dimers.

EXAMPLE II

The hydrogenation was carried out as described in Example I, but now 1.1 g $KOCH_3$ was used instead of $NaOCH_3$ and diaminobutane was used as solvent instead of diaminoethane. After 300 s the succinonitrile conversion was 100%. The reaction product consisted of 85 mol % aminobutyro nitrile, 14 mol % diaminobutane and 1 mol % pyrrolidine. The aminobutyronitrile yield was 85%.

EXAMPLE III

The hydrogenation was carried out as described in Example II, but now hexamethylene diamine was used as solvent in stead of diaminobutane. After 300 s the succinonitrile conversion was 100%. The reaction product consisted of 86.5 mol % aminobutyro nitrile, 13 mol % diaminobutane and <1 mol % pyrrolidine. The aminobutyro nitrile yield was 86.5%.

To study the hydrogenation kinetics, during the reaction a small sample was drawn from the reactor every 15 s and was analyzed. For reactions (1) and (2) first-order kinetics were observed, with $k_1=0.013$ and $k_2=8.1*10^{-4}$ $s^{-1}$. The $k_1/k_2$ ratio was 16.

COMPARATIVE EXPERIMENT B

Comparative example A was repeated, now the reaction kinetics being determined as described in Example III. First-order kinetics were observed for reactions (1) and (2), with $k_1=0.013$ and $k_2=2.2*10^{-3}$ $s^{-1}$. The $k_1/k_2$ ratio was 5.6.

EXAMPLE IV

The hydrogenation was carried out as described in Example I, but now adiponitrile was hydrogenated. In place of $NaOCH_3$, 1.2 g $KOCH_3$ was added. The water content of the catalyst slurry was 0.46 wt. %. After 180 s the adiponitrile conversion was 95%. The reaction product consisted of 77 mol % ε-aminocapronitrile and 23 mol % diaminohexane. The ε-aminocapronitrile yield was 73%.

To study the hydrogenation kinetics, after every 15 s of the reaction time a small sample was drawn from the reactor, which was analyzed. For reactions (1) and (2) first-order kinetics were observed, with $k_1=0.017$ and $k_2=2.18*10^{-3}$ $s^{-1}$. The $k_1/k_2$ ratio was 6.

COMPARATIVE EXPERIMENT C

The hydrogenation was carried out as described in Example IV. Use was made of a catalyst in water, which resulted in a water content of 11.2 wt % in the reaction mixture. After 90 s the adiponitrile conversion amounted to 99%. The reaction product consisted of 51 mol % ε-aminocapronitrile and 49 mol % hexamethylene diamine. The ε-aminocapronitrile yield was 51%.

To study the hydrogenation kinetics, during the reaction a small sample was drawn from the reactor, every 15 s and analyzed. For reactions (1) and (2) first-order kinetics were observed, with $k_1=0.051$ and $k_2=0.016$ s$^{-1}$. The $k_1/k_2$ ratio was 3.2.

We claim:

1. A process for preparing an aminonitrile comprising: partially hydrogenating a nitrile compound having at least two nitrile groups with hydrogen under a partial hydrogen pressure of at least 0.1 MPa to 50 MPa at a temperature of 0° to 200° C. in a reaction medium having less than 5 wt. % water using a catalyst containing a metal from group 8 of the periodic table of elements which is selected from the group consisting of nickel, cobalt, platinum, palladium, and rhodium, wherein the catalyst has been contacted with 0.01 to 0.5 gram of an alkanolate per gram of catalyst and said nitrile compound is an α,ω-alkane dinitrile or a dendrific macromolecule containing at least two nitrile groups.

2. The process according to claim 1, wherein said metal is Raney nickel or Raney cobalt which has been dehydrated.

3. The process according to claim 1, wherein said alkanolate contains 1 to 10 carbon atoms.

4. The process according to claim 1, wherein said alkanolate is in the form of a metal salt selected from the group consisting of alkali metal alkanolates and alkaline earth metal alkanolates.

5. The process according to claim 1, wherein said alkanolate is a methanolate or an ethanolate.

6. The process according to claim 1, wherein the hydrogenating is carried out such that the water content of the reaction medium is less than 1 wt. %.

7. The process according to claim 1, wherein said nitrile compound contains 3 to 12 carbon atoms and contains 3 or 4 nitrile groups.

8. The process according to claim 1, wherein said nitrile is malonitrile, succinonitrile, adiponitrile, or glutaronitrile.

9. The process according to claim 1, wherein said nitrile is succinonitrile or adiponitrile.

10. The process according to claim 1, wherein said nitrile is dissolved in a solvent prior to partially hydrogenating said nitrile.

11. The process according to claim 1, wherein said hydrogenating is carried out at a temperature of 20° to 100° C.

12. The process according to claim 1 or 11, wherein said hydrogenating is carried out at a partial hydrogen pressure of 3 to 10 MPa.

13. A process for preparing an aminonitrile comprising partially hydrogenating a nitrile compound having at least two nitrile groups with hydrogen gas at a partial hydrogen pressure of 3 to 10 MPa at a temperature of 20° C. to 100° C. to in the presence of less than 5 wt. % water in the presence of a catalyst containing a metal from group 8 of the periodic table of elements, wherein the catalyst has been treated with an alkanolate containing 1 to 10 carbon atoms and wherein said nitrile compound is (i) an α,ω-alkane dinitrile or (ii) a dendritic macromolecule containing at least two nitrile groups.

14. A process for preparing an aminonitrile comprising partially hydrogenating a nitrile compound having at least two nitrile groups with hydrogen gas in the presence of less than 5 wt. % water in the presence of a catalyst containing a metal from group 8 of the periodic table of elements, wherein the catalyst has been treated with an alkanolate and wherein said nitrile compound is (i) an α,ω-alkane dinitrile or (ii) a dendritic macromolecule containing at least two nitrile groups.

15. The process according to claim 13 or 14, wherein said metal is nickel, cobalt, platinum, palladium, or rhodium.

16. The process according to claim 14, wherein said metal is Raney nickel or Raney cobalt which has been dehydrated.

17. The process according to claim 14, wherein said alkanolate contains 1 to 10 carbon atoms.

18. The process according to claim 14, wherein said hydrogenating is carried out at a temperature of 20° to 100° C.

19. The process according to claim 14 or 18, wherein said hydrogenating is carried out at a partial hydrogen pressure of 3 to 10 MPa.

20. The process according to claim 14, wherein said alkanolate is in the form of a metal salt selected from the group consisting of alkali metal alkanolates and alkaline earth metal alkanolates.

21. The process according to claim 14, wherein said alkanolate is a methanolate or an ethanolate.

22. The process according to claim 21, wherein said alkanolate is sodium or potassium methanolate.

23. The process according to claim 13 or 14, wherein the catalyst has been treated with 0.01 to 0.5 gram of said alkanolate per gram of catalyst.

24. The process according to claim 14, wherein the catalyst has been treated with 0.03 to 0.2 gram of said alkanolate per gram of catalyst.

25. The process according to claim 14, wherein the catalyst has been treated with 0.05 to 0.15 gram of said alkanolate per gram of catalyst.

26. The process according to claim 1, 13 or 14, wherein said catalyst is rendered water-free and then treated with said alkanolate.

27. The process according to claim 14, wherein said nitrile compound contains 3 to 12 carbon atoms and contains 3 or 4 nitrile groups.

28. The process according to claim 14, wherein said nitrile is malonitrile, succinonitrile, adiponitrile, or glutaronitrile.

29. The process according to claim 14, wherein said nitrile is succinonitrile or adiponitrile.

30. The process according to claim 13 or 14, wherein the hydrogenating is conducted in the presence of less than 1 wt. % water.

31. The process according to claim 14, wherein the hydrogenating is carried out in a solvent selected from the group consisting of tetrahydrofuran, dioxane, an alkane (di)amine, an alcohol and an ether.

32. The process according to claim 31, wherein said solvent is an α,ω-alkane diamine or an alcohol having 1 to 10 carbon atoms.

33. The process according to claim 32, wherein said solvent is selected from the group consisting of diaminoethane, diaminobutane, methanol, ethanol, n-propanol, i-propanol, and n-butanol.

34. A process for preparing an aminonitrile comprising: partially hydrogenating an aliphatic nitrile compound having at least two nitrile groups with hydrogen under a partial hydrogen pressure of at least 0.1 MPa to 50 MPa at a temperature of 0° to 200° C. in a reaction medium having less than 5 wt. % water using a catalyst containing a metal from group 8 of the periodic table of elements which is selected from the group consisting of nickel, cobalt, platinum, palladium, and rhodium, wherein the catalyst has been contacted with 0.01 to 0.5 gram of an alkanolate per gram of catalyst.

* * * * *